(12) United States Patent
Hölscher et al.

(10) Patent No.: US 10,920,170 B2
(45) Date of Patent: Feb. 16, 2021

(54) FRAGRANCE MIXTURES CONTAINING TRICYCLO[5.2.1.0]-DECANE-8-ETHYL ETHER

(71) Applicant: SYMRISE AG, Holzminden (DE)

(72) Inventors: Bernd Hölscher, Halle (DE); Marc Mansfeld, Brevörde (DE); Tobias Wagner, Hellental (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/493,019

(22) PCT Filed: Mar. 21, 2017

(86) PCT No.: PCT/EP2017/056711
§ 371 (c)(1),
(2) Date: Sep. 11, 2019

(87) PCT Pub. No.: WO2018/171872
PCT Pub. Date: Sep. 27, 2018

(65) Prior Publication Data
US 2020/0063063 A1    Feb. 27, 2020

(51) Int. Cl.
| | | |
|---|---|---|
| *A61K 8/00* | (2006.01) |
| *C11B 9/00* | (2006.01) |
| *A61K 8/33* | (2006.01) |
| *A61Q 5/02* | (2006.01) |
| *A61Q 19/10* | (2006.01) |
| *C11D 3/50* | (2006.01) |

(52) U.S. Cl.
CPC .............. *C11B 9/0042* (2013.01); *A61K 8/33* (2013.01); *A61Q 5/02* (2013.01); *A61Q 19/10* (2013.01); *C11D 3/50* (2013.01)

(58) Field of Classification Search
CPC ................................ A61K 8/33; C11B 9/0042
See application file for complete search history.

(56) References Cited

FOREIGN PATENT DOCUMENTS

| DE | 3501888 C2 | 7/1988 |
|---|---|---|
| EP | 1591514 A2 | 11/2005 |

OTHER PUBLICATIONS

International Search Report and Written Opinion dated Aug. 3, 2017, for corresponding PCT Application No. PCT/EP2017/056711.
Japanese Office Action dated Oct. 19, 2020 for corresponding Japanese Application No. 2019-552224.

*Primary Examiner* — John R Hardee
(74) *Attorney, Agent, or Firm* — Polsinelli PC

(57) ABSTRACT

Described is in particular a fragrance mixture, preferably perfume oil, comprising the components (a) (tricyclo [5.2.1.0]-decane-8-ethyl ether)

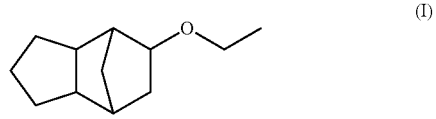

(I)

and additionally (b) one or more fragrance(s), preferably with a floral odor note, from the group consisting of alcohols and aldehydes having a molecular weight of 210 g/mol or less and/or (c) one or more fragrance(s) from the group consisting of ketones, ethers and esters having a molecular weight in the range from 190 g/mol to 250 g/mol. Furthermore, the present invention relates to methods for producing fragrance mixtures according to the invention, in particular perfume oils, perfumed products containing a fragrance mixture according to the invention, methods for producing perfumed products according to the invention as well as the use of the compound of formula (I) for enhancing the natural freshness and/or radiance and/or for masking or reducing greasy, technical and/or metallic notes of one or more fragrances different from the compound of formula (I).

18 Claims, No Drawings

FRAGRANCE MIXTURES CONTAINING TRICYCLO[5.2.1.0]-DECANE-8-ETHYL ETHER

CROSS-REFERENCE TO RELATED APPLICATIONS

This application is a national stage application (under 35 U.S.C. § 371) of PCT/EP2017/056711, filed Mar. 21, 2017, which is incorporated herein by reference in its entirety.

The present invention relates primarily to certain fragrance mixtures, preferably perfume oils, comprising a compound of formula (I) (tricyclo[5.2.1.0]-decane-8-ethyl ether)

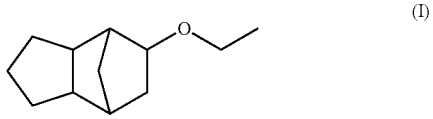
(I)

as well as one or more other specific fragrances (as described herein).

Furthermore, the present invention concerns methods for producing fragrance mixtures according to the invention, in particular perfume oils, perfumed products containing a fragrance mixture according to the invention, methods for producing perfumed products according to the invention and the use of the compound of formula (I) for enhancing the natural freshness and/or radiance and/or for masking or reducing greasy, technical and/or metallic notes of one or more fragrances different from the compound of formula (I).

Further aspects and preferred embodiments of the present invention can be derived from the following descriptions, the appended examples and, in particular, the appended patent claims.

The compound of formula (I) is known to a person skilled in the art (CAS No. 13213-08-6; see also Zhurnal Obshchei Khimii (1964), 34(6), 2081-4). A description of the odor of the compound of formula (I) can be found in DE 3501888 C2. The compound of formula (I) is described therein as strong, warm woody, strongly radiant and with a note reminiscent of forest leaves. In perfumery, the compound of formula (I) has not yet been used to any significant extent. Even a mixture of fragrances according to the invention (as described herein), let alone preferred or advantageous amounts (ratios), is not known in the state of the art. In particular, certain olfactory effects in combination with fragrances of components (b) or (c) (as described herein) have not yet been described.

According to the literature (Zhurnal Obshchei Khimii (1964), 34(6), 2081-4), the compound of formula (I) can be prepared e.g. by alkylation of tricyclo[5.2.1.0]-decan-8-ol by addition of ethanol to dicyclopentadiene and subsequent hydrogenation.

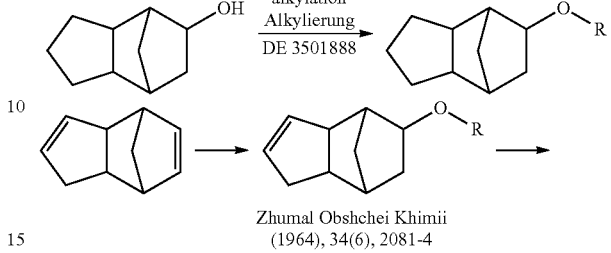

According to own experiments, ethanol can alternatively be added to dicyclopentadiene with acid ion exchangers (analogue to DE 2642519 A1) and then hydrogenated under hydrogen atmosphere:

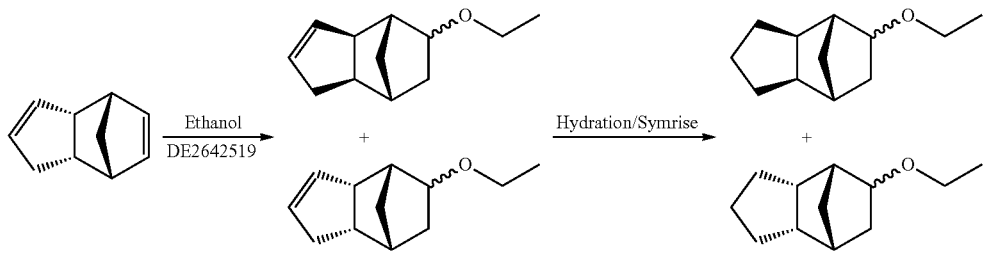

According to perfumers, the product produced in this way (cf. example 7 of the example section below) has the following olfactory characteristics: floral, green, fruity orange.

The compound of formula (I) to be used according to the invention (as described herein) may be provided in any stereoisomeric form or may be provided as any mixture of stereoisomers (e.g. exo/endo isomer mixture, diastereomer mixture, racemate). According to a preferred embodiment of the present invention (as described herein), it is provided as a mixture of two or more stereoisomers (cf. Example 7, Isomers I-IV (preferred combination of stereoisomers to be used according to the invention)).

Floral fragrances play an important role in perfumery. There is a constant need to emphasize certain olfactory aspects of a fragrance or fragrance mixture. In the case of floral fragrances, this is particularly true for their natural freshness and radiance. There is also a constant need to mask or reduce certain olfactory aspects of a fragrance or fragrance mixture. In the case of floral fragrances, this applies in particular to greasy, technical and metallic notes.

The primary objective of this invention was to identify new, beneficial fragrance mixtures. It was also an objective to emphasize certain olfactory aspects of certain fragrances or fragrance mixtures and/or to mask or reduce certain olfactory aspects of a fragrance or fragrance mixture, especially greasy and metallic notes.

According to the invention, the primary objective is solved by a mixture of fragrances, preferably a perfume oil, comprising the following components (a) Compound of formula (I)

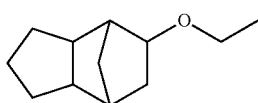

as well as additionally:
(b) one or more fragrance(s), preferably with a floral odor note, selected from the group consisting of alcohols and aldehydes having a molecular weight of 210 g/mol or less,
and/or
(c) one or more fragrance(s) selected from the group consisting of ketones, ethers and esters having a molecular weight ranging from 190 g/mol to 250 g/mol.

Fragrance mixtures according to invention are preferably liquid at 25° C. and 1013 hPa and are usually homogeneous solutions.

Surprisingly, in a mixture of fragrances according to the invention, the compound of formula (I) causes certain olfactory aspects of the fragrance(s) of the component (b) and/or of the fragrance(s) of the component (c) to be emphasized respectively highlighted and/or masked respectively reduced. In particular, fatty, technical and metallic notes of the fragrances of components (b) and/or (c) are effectively masked or reduced by the compound of formula (I).

A person skilled in the art can select the proportion of component (a), i.e. the proportion of the compound (I), in a mixture of fragrances (preferably a perfume oil) in accordance with the invention in such a way that the desired effect of emphasizing (accentuating) and/or masking respectively reducing an odor note is achieved, whereas he may take care, if necessary, not to use too large an amount of the component (a), which could dominate the overall sensory impression of a mixture of fragrances, and on the other hand not only to provide for such a small amount of the component (a) that an emphasis or masking/reduction of olfactory aspects of fragrances of the component (b) respectively (c) is not or hardly noticeable anymore. For preferred amount or concentration ratios, compare the following descriptions and the appended examples.

Surprisingly, the compound of formula (I) has been found to have additional positive secondary properties in addition to its primary sensory properties, such as high stability under certain conditions of use (in alkaline media (washing powder, fabric softener, soap, shampoo, etc.), high efficacy, good adhesion and high substantivity. This property is quite surprising for an ether with a molecular weight of 180 g/mol.

Component (b) of a Fragrance Mixture According the Invention:

Component (b) of the fragrance mixture according to the invention consists of or comprises one or more fragrances selected from the group consisting of alcohols and aldehydes having a molecular weight of 210 g/mol or less. Preferably, these fragrances have a floral odor note. Such fragrances are known to a person skilled in the art.

Preferred are fragrance mixtures according to the invention, preferably perfume oils, wherein the component (b) comprises or consists of two, three, four, five or more different fragrances.

Preferably, in a fragrance mixture according to the invention, the mass ratio of the total amount of the fragrance(s) of the component (b) to the compound of formula (I) is greater than or equal to 99:1, preferably greater than or equal to 99.9:0.1, particularly preferably greater than or equal to 99.999:0.001.

Own investigations have shown that these mass ratios are particularly advantageous. At these mass ratios, the inherent odor of the compound of formula (I) is regularly no longer perceptible or barely perceptible, but the presence of the compound of formula (I) has a positive effect on the overall note of the fragrance mixture according to the invention. It is particularly surprising that the compound of formula (I) has an effect on the freshness and radiance of the fragrance mixture, even in low concentrations, without causing or emphasizing a fruity odor to a relevant extent.

Particularly preferred are fragrance mixtures according to invention, preferably perfume oils according to invention, wherein the, one, more than one or all fragrances of component (b) is selected, respectively are selected from the group consisting of 2-methyl-3-(4-tert-butylphenyl)propanal, 4-(4-hydroxy-4-methylpentyl)-3-cyclohexenecarboxaldehyde, 2-methyl-4-(2,2,6-trimethyl-1-cyclohexen-1-yl)-2-butenal, 1-Methyl-4-(4-methyl-3-penten-1yl)-3-cyclohexenecarbox aldehyde, 3-(3-isopropyl-phenyl)-butyraldehyde, (E)-2,6,10trimethyl-undeca-5,9-dienal, benzo[1,3]dioxole-5-carbaldehyde, 2,2-di methyl-3-phenyl-propan-1-ol, 2,2-Dimethyl-3-m-tolyl-propan-1-ol, 1-(4-isopropyl-cyclohexyl)-ethanol, (4-isopropyl-cyclohexyl)-methanol, 2-phenyl-ethanol, 2-isobutyl-4-methyl-tetrahydro-pyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylenoct-7-en-2-ol and (E/Z)-3,7-dimethyl-nona-1,6-dien-3-ol.

Particularly preferred are fragrances according to invention, preferably perfume oils according to invention, where the one, more than one or all fragrances of the component (b) is selected respectively are selected from the group consisting of 1-(4-isopropylcyclohexyl)-ethanol (mugetanol), (E)-3,7-dimethyl-octa-2,6-dien-1-ol (geraniol), 3,7-dimethyl-oct-6-en-1-ol (citronellol), (4-isopropyl-cyclohexyl)-methanol (mayol), 2-methyl-6-methylenoct-7-en-2-ol (myrcenol) (2-methyl-6-methylenoct-7-en-2-ol) and 2,6-dimethyloct-7-en-2-ol (dihydromyrcenol).

Preferred are fragrance mixtures according to the invention, preferably perfume oils according to the invention, wherein the one, more than one or all fragrances of the component (b) (each) have a molecular weight in the range of 140 to 170 g/mol.

Particularly preferred are fragrance mixtures according to the invention, preferably perfume oils according to invention, in which the component (b) is an alcohol or contains an alcohol.

Surprisingly, the sensory properties of fragrances of the component (b) are positively influenced by combination with a compound of formula (I). In individual cases, the sensory impression is shifted in the direction of more natural, fresher, more flowery, more radiant, less technical, less greasy and/or less metallic, whereas other sensory influences were also observed in individual cases. Further descriptions of odors can be found in the appended examples.

Component (c) of a Fragrance Mixture of the Invention:

Preferred are fragrance mixtures according to the invention, preferably perfume oils, wherein the component (c) comprises or consists of two, three, four, five or more different fragrances.

The fragrance(s) of the component (c) regularly function(s) as fond note(s) of a fragrance mixture according to the invention or of a perfume oil according to the invention.

Preferably the fragrances of the component (c) are ketones, ethers and/or esters with a molecular weight in the range 196 g/mol to 250 g/mol.

Compounds having a molecular weight between 190 and 210 g/mol and belonging both to the group of aldehydes and/or alcohols and to the group of ketones, esters and/or ethers are assigned both to the component (b) and to the component (c).

Particularly preferred are fragrance mixtures according to the invention, preferably perfume oils according to the invention, wherein the mass ratio of the total amount of the fragrance(s) of the component (c) to the total amount of the compound of formula (I) is greater than or equal to 99:1, preferably greater than or equal to 99.9:0.1, particularly preferably greater than or equal to 99.999:0.001.

In own investigations it was found that these mass ratios are particularly advantageous. With these mass ratios, the inherent odor of the compound of formula (I) is regularly no longer perceptible or hardly perceptible, but the presence of the compound of formula (I) has a positive effect on the overall note of the fragrance mixture according to the invention. It is particularly surprising that the compound of formula (I) has an effect on the freshness and radiance of the fragrance mixture, even in low concentrations, without causing or emphasizing a relevant fruity odor.

Examples of fragrances with a molecular weight in the range of 190 g/mol to 250 g/mol which may be part of the component (c) are known to a person skilled in the art and can be found for example in S. Arctander, Perfume and Flavor Materials, Vol. I and II, Montclair, N. J., 1969, Selbstverlag or H. Surburg, J. Panten, "Common Fragrance and Flavor Materials", 5th. Ed., Wiley-VCH, Weinheim 2006.

Particularly preferred are fragrance mixtures according to invention, preferably perfume oils according to invention, wherein the fragrance or fragrances of the component (c) are selected from the group consisting of methyl dihydrojasmonate, benzylsalicylate, cis-3-hexenyl salicylate, isoamyl salicylate, hexyl salicylate, 2,3,8,8-tetramethyl-1,2,3,4,5,6,7,8-octahydro-2-naphthalenylmethylketone, linalyl acetate, ethyl linalyl acetate, cedryl methyl ether, cedryl methylketone, cedryl acetate, (4aR,5R,7aS,9R)-octahydro-2,2,5,8,8,9a-hexamethyl-4H-4a,9-methano azuleno(5,6-d)-1,3-dioxole), 1',1',5',5'-tetra methyl-hexahydro-spiro[1.3-dioxolane-2.8'(5'H)-2H-2.4a]methanonaphthalene, cyclododecyl methyl ether, (ethoxymethoxy)cyclododecane, decahydrobetanaphthyl acetate, 4,7-methano-3a,4,5,6,7,7a-hexahydro-5(-6)-indenyl acetate, allyl-3-cyclohexyl propionate, allyl cyclohexyloxy acetate, benzylbenzoate, benzylcinnamate, oxacyclohexa-decan-2-one, 15-hydroxy-pentadecanonic acid lactone, 5-cyclohexadecen-1-one, 3-methyl-cyclopentadecenone, 1,3,4,6,7,8-hexahydro-4,6,6,6,7,8,8-hexamethyl cyclopenta[g]-2-benzopyran, 2-[1-(3,3-dimethylcyclohexyl) ethoxy]-2-methyl-, 1-propanoate, 1,4-dioxacycloheptadecane-5,17-dione, 3-methycyclopentadecanone, 8-cyclohexadecen-1 one, 3a,6,6,9a-tetramethyl dodecahydronaphtho[2,1-b]furan, alpha-iron, beta-iron, alpha-n-methylionone, beta-n-methylionone, alpha-isomethylionone, beta-isomethylionone and allylionone.

Surprisingly, the sensory properties of the fragrances of the component (c) are positively influenced by combination with a compound of formula (I). In individual cases, the sensory impression is shifted in the direction of more natural, fresher, more flowery, more radiant, less greasy and/or less metallic, whereas in individual cases other sensory influences were of course also observed. Further descriptions of odors can be found in the appended examples.

In fragrance mixtures according to the invention, the compound of formula (I) is preferably used in at least such an amount that a sensory effect is achieved (sensory effective amount). A sensory effect is achieved by the presence of the compound of formula (I) if a comparative fragrance mixture which does not contain a compound of formula (I) with an otherwise identical composition is evaluated sensorially differently from the fragrance mixture according to the invention.

The compound of the formula (I) is preferably used in a fragrance mixture according to the invention in such a concentration that the sensory impression of the fragrance mixture according to the invention is more natural, fresher, more flowery, more radiant, less greasy, less technical and/or less metallic than the sensory impression of a comparative fragrance mixture which, with an otherwise identical composition, does not contain a compound of the formula (I).

Preferably, the mass ratio of the total amount of fragrances of components (b) and/or (c) to the total amount of compound of formula (I) is less than or equal to 99.999: 0.0001.

Fragrance mixtures according to the invention, in particular perfume oils according to the invention, can be used in liquid form, undiluted or diluted with a solvent for perfuming or flavoring. Suitable solvents are in particular ethanol, glycerol, 1,2-propylene glycol, 1,2-butylene glycol, dipropylene glycol, diethyl phthalate, triethyl citrate, isopropyl myristate and triacetin.

Alcohols and aldehydes having a molecular weight of 210 g/mol or less as well as ketones, ethers and esters having a molecular weight in the range of 190 g/mol to 250 g/mol are not counted as components (b) or (c), respectively, provided that they are a compound selected from the group consisting of ethanol, isopropanol, glycerol, 1,2-propylene glycol, 1,2-butylene glycol, dipropylene glycol, diethyl phthalate and triacetin.

Preferably, fragrance mixtures according to the invention, preferably perfume oils according to the invention, are combined with other components, e.g. to produce products according to the invention described herein. Preferred other components are selected from the group consisting of:

Preservatives, preferably those mentioned in US 2006/0089413, abrasives, anti-acne agents and sebum reducing agents, preferably those mentioned in WO 2008/046791, anti-aging agents, preferably those mentioned in WO 2005/123101, antibacterial agents, anti-cellulite agents, anti-dandruff agents, preferably those mentioned in WO 2008/046795, anti-inflammatory agents, anti-irritants (anti-inflammatory, irritation-inhibiting and irritation-preventing agents), preferably those mentioned in WO 2007/042472 and US 2006/0089413, antimicrobial agents, preferably those mentioned in WO 2005/123101, antioxidants, preferably those mentioned in WO 2005/123101, astringents, antiseptic agents, antistatic agents, binders, buffers, carrier materials, preferably those mentioned in WO 2005/123101, chelating agents, preferably those mentioned in WO 2005/123101, cell stimulants, cleaning agents, caring agents, depilatories, surfactants, deodorants and antiperspirants, preferably those mentioned in WO 2005/123101, plasticizers, emulsifiers, preferably those mentioned in WO 2005/123101, enzymes, essential oils, preferably those mentioned in US 2008/0070825, insect repellents, preferably those mentioned in WO 2005/123101, fibers, film formers, fixers, foaming agents, foam stabilizers, foaming inhibitors, foam boosters, fungicides, gelling agents and gelling agents, preferably those mentioned in WO 2005/123101, hair care products, hair deforming agents, hair straightening agents, moisture regulators (moisturizing, moistening and/or moisture-retaining substances), preferably those mentioned in WO 2005/123101, osmolytes, preferably those mentioned in WO 2005/123101, compatible solutes, preferably those mentioned in WO 01/76572 and WO 02/15686, bleaching agents, strengthening agents, stain removing agents, optical whitening agents, impregnating agents, dirt-repellent agents, friction-reducing agents, lubricants, moisturizing creams, ointments, opacifiers, plasticizers, opacifiers, polishable agents, glazing agents, polymers, preferably those mentioned in WO 2008/046676, powders, proteins and protein hydrolysates, preferably those mentioned in WO 2005/123101 and WO 2008/046676, refatting agents, abrasive agents, skin-soothing agents, skin-cleaning agents, skin-care agents, skin repair agents, preferably containing cholesterol and/or fatty acids and/or ceramides and/or pseudo ceramides, preferably those mentioned in WO 2006/053912, skin brightening agents, preferably those mentioned in WO 2007/110415, skin protecting agents, skin softening agents, skin cooling agents, preferably those mentioned in WO 2005/123101, skin warming agents, preferably those mentioned in WO 2005/123101, stabilizers, UV absorbing agents and UV filters, preferably those mentioned in WO 2005/123101, benzylidene-betadicarbonyl compounds, preferably those mentioned in WO 2005/107692, alpha-benzoyl cinnamic acid nitriles, preferably those mentioned in WO 2006/015954, AhR receptor antagonists, preferably those mentioned in WO 2007/128723 and WO 2007/060256, laundry detergents, fabric softeners, suspending agents, skin tanning agents, preferably those mentioned in WO 2006/045760, thickeners, vitamins, preferably those mentioned in WO 2005/123101, oils, waxes and fats, preferably those mentioned in WO 2005/123101, phospholipids, preferably those mentioned in WO 2005/123101, fatty acids (saturated fatty acids, monounsaturated or polyunsaturated fatty acids, α-hydroxy acids, polyhydroxy fatty acids), preferably those mentioned in WO 2005/123101, plasticizers, dyes and color protecting agents as well as pigments, preferably those mentioned in WO 2005/123101, anticorrosives, flavors and fragrances as well as other additional fragrances, preferably those mentioned in S. Arctander, Perfume and Flavor Chemicals, self-published, Montclair, N.J., 1969 and Surburg, Panten, Common Fragrance and Flavor Materials, 5th Edition, Wiley-VCH, Weinheim 2006, in particular the further fragrances explicitly mentioned in US 2008/0070825, which are not already part of components (b) and (c) of a fragrance mixture respectively of a perfume oil according to the invention, alcohols and polyols, preferably those mentioned in WO 2005/123101, surfactants, preferably those mentioned in WO 2005/123101, animal extracts, yeast extracts, extracts of algae or microalgae, electrolytes, liquefiers, organic solvents, preferably those mentioned in WO 2005/123101, or silicones and silicone derivatives, preferably those mentioned in WO 2008/046676. However, compounds falling under the definition of components (b) and/or (c) are assigned to these components regardless of their intended use; for exemptions for certain solvents see above.

Furthermore, fragrance mixtures according to the invention, in particular perfume oils according to the invention, may be adsorbed on a carrier which ensures both a fine distribution of the fragrances contained therein in the product and a controlled release during application. Such carriers may be porous inorganic materials such as light sulphate, silica gels, zeolites, gypsums, clays, clay granules, gas concrete, etc. or organic materials such as wood, cellulose-based materials, sugar, dextrins (e.g. maltodextrin) or plastics such as PVC, polyvinyl acetates or polyurethanes. The combination of a fragrance mixture in accordance with the invention and a carrier substance is an exemplary product in accordance with the invention (as described herein).

Fragrance mixtures according to invention, especially perfume oils according to the invention, can also be microencapsulated, spray-dried, provided as inclusion complexes or as extrusion products (i.e. products according to the invention) and can be added in this form e.g. to a product to be perfumed (also according to invention).

The properties of such modified compositions may be further optimized by so-called "coating" with suitable materials with a view to a more targeted release of fragrance, for which wax-like plastics such as polyvinyl alcohol are preferably used. The resulting products in turn represent products according to the invention.

The microencapsulation of the fragrance mixtures in accordance with the invention, preferably the perfume oils in accordance with the invention, can be achieved, for example, by the so-called coacervation process with the aid of capsule materials, e.g. made of polyurethane-like substances or soft gelatin.

Spray-dried perfume mixtures can be prepared, for example, by spray-drying an emulsion respectively dispersion containing the fragrance mixture according to the invention, preferably a perfume oil, wherein modified starches, proteins, dextrin and vegetable gums can be used as carriers.

Inclusion complexes may be prepared, for example, by incorporating dispersions of the fragrance mixture according to the invention, preferably a perfume oil according to the invention, and cyclodextrins or urea derivatives into a suitable solvent, e.g. water.

Extrusion products may be obtained by fusing a fragrance mixture according to the invention, preferably a perfume oil according to the invention, with a suitable wax-like substance and by extrusion followed by solidification, if necessary, in a suitable solvent, e.g. isopropanol.

The invention further relates to a method for producing a fragrance mixture, preferably a perfume oil, as described herein, comprising or consisting of the following step:

mixing component (a) with component (b) and/or component (c).

A method is preferred, wherein a fragrance mixture, preferably a perfume oil, is obtained in which the mass ratio of the total amount of the fragrance(s) of the component (b) to the total amount of the compound of formula (I) is greater than or equal to 99:1, preferably greater than or equal to 99.9:0.1, more preferably greater than or equal to 99.999:0.001, and/or the mass ratio of the total amount of the fragrance(s) of the component (c) to the total amount of the compound of formula (I) is greater than or equal to 99:1, preferably greater than or equal to 99.9:0.1, more preferably greater than or equal to 99.999:0.001.

It has been shown that the respective mass ratios are particularly advantageous. Reference is made to the above explanations.

In addition, the above mentioned in connection with fragrance mixtures in accordance with the invention and, in particular, with preferred fragrance mixtures in accordance with the invention shall apply mutatis mutandis to preferred embodiments of this method.

The invention further relates to a method of enhancing the natural freshness and/or radiance and/or masking or reducing greasy, technical and/or metallic notes of one or more fragrances other than the compound of formula (I), in particular one or more fragrances other than the compound of formula (I), with a floral odor note of odor, in particular jasmine, comprising the following step:

Mixing the fragrance(s) other than the compound of formula (I) with an amount of the compound of formula (I) sufficient to enhance the natural freshness and/or radiance of the fragrance(s) other than the compound of formula (I) and/or to mask or reduce greasy, technical and/or metallic notes.

Preferred is a method according to the invention in which the fragrance(s) other than the compound of formula (I) is/are selected from the components (b) and/or (c) of a fragrance mixture according to the invention (as described herein).

In such preferred methods it is preferable that
the mass ratio of the total amount of fragrance(s) of the component (b) to the total amount of the compound of formula (I) is greater than or equal to 99:1, preferably greater than or equal to 99.9:0.1, more preferably greater than or equal to 99.999:0.001,
and/or
the mass ratio of the total amount of the fragrance(s) of the component (c) to the total amount of the compound of formula (I) is greater than or equal to 99:1, preferably greater than or equal to 99.9:0.1, particularly preferably greater than or equal to 99.999:0.001.

The above explanations concerning preferred fragrance mixtures according to the invention also apply mutatis mutandis to such a method according to the invention.

The invention also relates to a perfumed product containing a fragrance mixture according to the invention, preferably a perfume oil according to the invention, wherein the fragrance mixture is preferably contained in a sensory effective amount in the perfumed product. "Sensory effective amount" in the present context means that the perfumed product according to the invention reveals the sensory properties of the fragrance mixture according to the invention during operation respectively use.

Preferred perfumed products according to the invention are selected from the group consisting of: Perfume extracts, eau de parfums, eau de toilettes, shaving lotions, eau de colognes, pre-shave products, splash colognes, perfumed refreshing wipes, acidic, alkaline and neutral cleaning agents, textile fresheners, ironing aids, liquid laundry detergents, powdered laundry detergents, laundry pre-treatment agents, fabric softeners, laundry soaps, wash tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants and antiperspirants, decorative cosmetic products, candles, lamp oils, incense sticks, insecticides, repellents and fuels.

Particularly preferred perfumed products according to the invention are selected from the following list:
Eau de Parfums, Eau de Toilettes, After-shave, Eau de Colognes, Pre-shave products, Splash-Colognes;
Acidic, alkaline and neutral cleaning agents, especially for household use, preferably floor cleaners, window glass cleaners, dishwashing detergents, bathroom and sanitary cleaners, scouring lotions, solid and liquid WC cleaners, powdery and foamy carpet cleaners, liquid laundry detergents, powdery laundry detergents, fabric softeners, surface disinfectants, especially for hard surfaces (hard surface cleaners);
Body care products, preferably solid and liquid soaps, shower gels, shampoos, shaving soaps, shaving foams;
Cosmetic emulsions of the oil-in-water, water-in-oil and water-in-oil-in-water type, preferably skin creams and lotions, face creams and lotions, sunscreens and lotions, after-sun creams and lotions, hand creams and lotions, foot creams and lotions, depilatory creams and lotions, after-shave creams and lotions, skin tanning creams and lotions, skin lightening creams and lotions;
Hair care products, preferably hair sprays, hair gels, firming hair lotions, hair conditioners, permanent and semi-permanent hair dyes, hair tonics, hair creams and lotions;
Deodorants and antiperspirants, preferably underarm sprays, roll-ons (preferably as alcoholic or non-alcoholic solution, as gel or (micro)emulsion, deodorant sticks, deodorant creams.

Particularly preferred perfumed products according to the invention are laundry detergents and cleaning agents, hygiene or care products, especially in the field of body and hair care, cosmetics and the household.

Preferred perfumed products according to the invention are those in which the proportion of the fragrance mixture according to the invention or the proportion of the total quantity of the components (a), (b) and/or (c) together in the perfumed product is 0.01 to 10% by weight, preferably 0.1 to 5% by weight and more preferably 0.25 to 3% by weight, in each case based on the total mass of the perfumed product. This applies in particular to the preferred products mentioned above.

The invention also relates to a method of producing a perfumed product consisting of or comprising the following steps:
i) providing a fragrance mixture in accordance with the invention (as described herein) or producing a fragrance mixture by a method in accordance with the invention (as described herein), preferably wherein the component or the components (b) and/or (c) are present in a sensory effective amount,
ii) providing one or more other components of the perfumed product to be produced and
iii) contacting or mixing the further component(s) provided in step (ii) with a sensory effective amount of the fragrance mixture provided in step (i),
preferably wherein the amount of the compound of formula (I) is sufficient to enhance the natural freshness and/or radiance of one, more than one or all of the fragrances of components (b) and/or (c) and/or to mask or reduce greasy, technical and/or metallic notes,
or
I) providing one or more components of the perfumed product to be produced which are not the components (a), (b) or (c) of a fragrance mixture according to the invention (as described herein),
II) mixing the component(s) provided in step I) with the components (b) and/or (c) of a fragrance mixture according to the invention (as described herein) so as to result in a mixture in which the component(s) (b) and/or (c) are present in a sensory effective amount,
III) contacting or mixing the mixture prepared in step II) with an amount of the compound of formula (I), wherein the amount of the compound of formula (I) is sufficient to enhance the natural freshness and/or radiance of one, more than one or all of the fragrances of components (b) and/or (c) and/or to mask or reduce greasy, technical and/or metallic notes.

The above remarks in respect of preferred fragrance mixtures according to the invention also apply mutatis mutandis to such a method according to the invention.

Finally, the invention also relates to the use of a compound of formula (I)

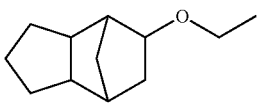
(I)

for enhancing the natural freshness and/or radiance and/or for masking or reducing greasy, technical and/or metallic notes of one or more fragrances other than the compound of formula (I), in particular with a floral odor note, preferably jasmine,
wherein preferably the fragrance or fragrances other than the compound of formula (I) is or are selected from the components (b) and/or (c) of a fragrance mixture according to the invention (as described herein).

Preferred is a use according to the invention of the compound of formula (I), wherein the fragrance or fragrances other than the compound of formula (I) are selected from the components (b) and/or (c) of a fragrance mixture according to the invention.

Again, the above remarks in respect of preferred fragrance mixtures according to the invention shall apply mutatis mutandis.

The following examples illustrate the present invention and preferred aspects thereof. Unless otherwise stated, proportions and percentages refer to weight.

EXAMPLES

Abbreviations used: Dipropylene glycol (DPG), diethyl phthalate (DEP), triethyl citrate (TEC), isopropyl myristate (IPM); nat.=natural.

HEDIONE® (HC/30) contains at least 30% by weight of the cis isomer and nearly 70% by weight of the trans-isomer of methyldihydrojasmonat.

For explanations of product names of fragrances refer to e.g. S. Arctander, Perfume and Flavor Materials, Vol. I and II, Montclair, N. J., 1969, self-published or H. Surburg, J. Panten, "Common Fragrance and Flavor Materials", 5 th. Ed., Wiley-VCH, Weinheim 2006.

1 Example: Perfume Oil P1

| Preferred application: | All-purpose cleaner 0.4% |
|---|---|
| Aldehyde C 8 | 20.00 |
| Aldehyde C11 MOA | 10.00 |
| Limonenal | 2.00 |
| Mintonat | 120.00 |
| Dihydro myrcenol | 50.00 |
| Lemon oil | 10.00 |
| Litesea cubeba oil | 40.00 |
| Citronitrile | 10.00 |
| Eucalyptus oil citriodora | 50.00 |
| Citronella oil | 40.00 |

-continued

| Preferred application: | All-purpose cleaner 0.4% |
|---|---|
| Orange oil | 130.00 |
| Terpineol | 20.00 |
| Lavandin oil | 50.00 |
| Rosemary oil | 5.00 |
| Eucalyptus oil | 5.00 |
| Aromabase apple green | 20.00 |
| Rosaphen ® | 20.00 |
| Benzyl acetate | 150.00 |
| Coumarin | 20.00 |
| Timberide | 2.00 |
| Dipropylene glycol | 226.00 |
| | 1,000.00 |

With addition of 0.5% of a 1% solution (in DPG) of tricyclo[5.2.1.0]-decane-8-ethyl ether the mixture becomes rounder, more harmonious, more natural, stronger and less technical.

With addition of 1% of a 1% solution (in DPG) of tricyclo[5.2.1.0]-decane-8-ethyl ether, the mixture becomes stronger in the top note and gives an additional mandarin note.

2. Example: Perfume Oil P2

| Preferred application: | Shower gel 0.5% |
|---|---|
| Limonenal 10% | 4.00 |
| Florazon | 1.00 |
| Leafovert ® | 6.00 |
| Vertocitral | 14.00 |
| Phenylacetald. dimethyl acetal | 10.00 |
| Cyclogalbant ® | 10.00 |
| Floropal | 7.00 |
| Mintonat | 50.00 |
| Lemongrass oil rect. | 8.00 |
| Orange oil | 40.00 |
| Claritone ® | 15.00 |
| Rosemary oil | 5.00 |
| Artemisia oil | 5.00 |
| Thyme oil white | 1.00 |
| Pine needle oil | 4.00 |
| Hexyl acetate | 20.00 |
| Ethyl methyl butyrate-2 | 2.00 |
| Allyl cyclohexyl propionate | 3.00 |
| Peach total | 1.00 |
| Melon concentrate | 12.00 |
| Lilax soft | 100.00 |
| Linalool | 55.00 |
| Geranium RCO | 7.00 |
| Phenylethyl alcohol | 60.00 |
| Geraniol supra | 70.00 |
| Geranyl acetate pure | 20.00 |
| Benzyl acetate | 24.00 |
| Hedione | 90.00 |
| Hexyl cinnamic aldehyde alpha | 60.00 |
| Hexenyl salicylate Cis-3 | 60.00 |
| Parmanyl ® | 3.00 |
| Isoeugenol | 2.00 |
| Coumarin | 3.00 |
| Vetikolacetat ® | 2.00 |
| Corps racine 0.1% | 7.00 |
| Evernyl 10% | 14.00 |
| Ambrettolide | 5.00 |
| Globanone ® | 90.00 |
| Dipropylene glycol | 110.00 |
| Triethyl citrate | |
| | 1,000.00 |

With addition of 0.5% of a 1% solution (in DPG) of tricyclo[5.2.1.0]-decane-8-ethyl ether, the mixture becomes rounder and fresher.

By adding 1% of a 1% solution (in DPG) of tricyclo [5.2.1.0]-decane-8-ethylether, the mixture becomes more floral and more towards white flower.

3. Example: Perfume Oil P3

| Preferred application: | Fabric softener 0.8% |
|---|---|
| Aldehyde C11 undecylenic 10% | 15.00 |
| Florazon | 10.00 |
| Mintonat | 10.00 |
| Dihydro myrcenol | 40.00 |
| Mandaril 10% | 10.00 |
| Orange Oil | 70.00 |
| Nerolione 10% | 15.00 |
| Majantol ® | 60.00 |
| Tetrahydro linalool | 50.00 |
| Phenylethyl alcohol | 70.00 |
| Citronellol 950 | 50.00 |
| Citronellyl acetate extra | 20.00 |
| Isodamascon ® 10% | 10.00 |
| Benzyl acetate | 30.00 |
| Hedione | 30.00 |
| Hexyl cinnamic aldehyde alpha | 20.00 |
| Hexyl salicylate | 100.00 |
| Eugenol | 10.00 |
| Heliotropin | 20.00 |
| Ethyl vanillin 10% | 30.00 |
| Herbyl propionate | 100.00 |
| Iso E super | 100.00 |
| Patchouli oil | 10.00 |
| Timberide | 5.00 |
| Corps racine 0.1% | 7.00 |
| Evernyl 10% | 5.00 |
| Galaxolide type base | 100.00 |
| Triethyl citrate | 3.00 |
| | 1,000.00 |

By adding 0.5% of a 1% solution (in DPG) of tricyclo [5.2.1.0]-decane-8-ethyl ether the mixture becomes rounder, less technical and more natural.

By adding 1% of a 1% solution (in DPG) of tricyclo [5.2.1.0]-decane-8-ethylether, the mixture becomes more flowery and more towards white flower.

4. Example: Perfume Oil P4

| Preferred application: | Fabric softener 0.8% |
|---|---|
| Aldehyde C12 | 5.00 |
| Alcohol C 6 | 10.00 |
| Dihydro myrcenol | 30.00 |
| Claritone ® | 10.00 |
| Petitgrain oil parag. | 5.00 |
| Methyl naphtyl ketone beta cryst | 10.00 |
| Lavandin grosso | 20.00 |
| Rosemary oil tun. | 10.00 |
| Hexyl acetate | 5.00 |
| Cyclamen aldehyde | 10.00 |
| Mugetanol ® | 40.00 |
| Majantol ® | 30.00 |
| Tetrahydro muguol | 20.00 |
| Base muguet B | 20.00 |
| Tetrahydro linalool | 40.00 |
| Dimethyl benzyl carbinyl acetate | 30.00 |
| Terpineol pure | 20.00 |
| Rose oxide HC 10% | 20.00 |
| Phenyl ethyl alcohol | 60.00 |

-continued

| Preferred application: | Fabric softener 0.8% |
|---|---|
| Base rose pamela-Y | 30.00 |
| Tetrahydrogeraniol | 10.00 |
| Isodamascon ® 10% | 20.00 |
| Benzyl acetone | 40.00 |
| Hexyl salicylate | 140.00 |
| Parmanyl ® 10% | 10.00 |
| Ionone beta | 10.00 |
| Isoraldeine | 50.00 |
| Base ylang B | 15.00 |
| Anisic aldehyde pure | 10.00 |
| Herbaflorat | 30.00 |
| Herbyl proprionate | 60.00 |
| Iso E Super | 120.00 |
| Sandel 80 | 20.00 |
| Ysamber ® K | 10.00 |
| Globanone ® | 30.00 |
| Dipropylene glycol | |
| | 1000.00 |

By adding 0.5% of a 1% solution (in DPG) of tricyclo [5.2.1.0]-decane-8-ethyl ether to the mixture, the mixture becomes rounder, more flowery and goes in the direction of lavender.

By adding 1% of a 1% solution (in DPG) of tricyclo [5.2.1.0]-decane-8-ethylether, the mixture becomes more voluminous and acts more strongly towards white flowering.

5. Example: Perfume Oil P5

| Preferred application: | Body Lotion 0.3% |
|---|---|
| Aldehyde C14 SOG | 5.00 |
| Allylamylglycolat | 2.00 |
| Allylcyclohexylpropionate | 2.00 |
| Allylheptylate | 5.00 |
| Allylionone | 1.00 |
| Ambroxide 10% IPM | 4.00 |
| Benzyl acetate | 2.00 |
| Benzyl salicylate | 21.50 |
| Bourgeonal | 4.00 |
| Damascon alpha 10% DPG | 1.00 |
| Dihydromyrcenol | 20.00 |
| Dimethyl benzylcarbinyl acetate | 10.00 |
| Farenal | 1.00 |
| Frambinon 10% DPG | 3.00 |
| Geranylacetate pure | 4.00 |
| Hedion | 200.00 |
| Indoflor crist 10% DPG | 5.50 |
| Ionone alpha | 10.00 |
| Iso e super | 40.00 |
| Jasmon cis | 1.00 |
| Leafovert | 2.00 |
| Macrolide supra | 30.00 |
| Majantol | 50.00 |
| Manzanate 10% IPM | 4.00 |
| Mayol | 55.00 |
| Methylphenylacetate 10% DPG | 2.00 |
| Mintonat | 5.00 |
| Nonadienal trans. | 2.00 |
| cis-2.6 5% TEC 1% DPG | |
| Patchouli oil | 2.00 |
| Phenylethyl alcohol | 15.00 |
| Phenylethyldimethylcarbinol | 7.00 |
| Roseaphene | 20.00 |
| Rose oxidi L 1% DPG | 5.00 |
| Sandranol | 5.00 |
| Tetrahydromuguol | 40.00 |
| Undecavertol | 2.00 |
| Veloutone 10% DPG | 3.00 |

-continued

| Preferred application: | Body Lotion 0.3% |
|---|---|
| Vertocitral | 2.00 |
| Vertomugual | 1.00 |
| Dipropylene glycol | 406.00 |
| | 1,000.00 |

By adding 0.5% of a 1% solution (in DPG) of tricyclo[5.2.1.0]-decane-8-ethyl ether the mixture becomes rounder, fresher and more natural.

By adding 1% of a 1% solution (in DPG) of tricyclo[5.2.1.0]-decane-8-ethylether, the mixture becomes more voluminous and acts more strongly in the direction of white flower (jasmine).

6. Example: Description of Odor of Preferred Fragrances after Addition of Tricyclo[5.2.1.0]-Decane-8-Ethyl Ether

| Fragrance | Type | Mass ratio of the fragrance to the compound of formula (I) (1% in DPG) | Odor description in comparison to the odor of the pure fragrance |
|---|---|---|---|
| Mugetanol (M = 170) | Alcohol | 99:1.0 | softer, more natural, more flowery, more radiant not so greasy, not so earthy |
| Dihydro-myrcenol (M = 156) | Alcohol | 99:1.0 | less unpleasant top note, more natural lavender-like, more flowery |
| Linalool (M = 154) | Alcohol | 99:1.0 | less metallic top note, fresher, more natural |
| Geraniol (M = 154) | Alcohol | 99:1.0 | less greasy, less metallic, rounder, stronger, more natural, more volume |
| Citronellol (M = 156) | Alcohol | 99:1.0 | less greasy, rounder, natural, more floral |
| Phenoxanol (M = 178) | Alcohol | 99:1.0 | less greasy, more floral, more natural |
| Lilial ® (M = 204) | Aldehyde | 99:1.0 | less metallic, fresher, more natural, stronger like lily of the valley |
| Aldehyd MNA (M = 184) | Aldehyde | 99:1.0 | less greasy, less metallic, clear, brighter, rounder |
| Melonal ® (M = 140) | Aldehyde | 99:1.0 | less metallic, rounder, more natural, more aldehydeic, cleaner |
| Hedion ® (M = 226) | Ketone/Ester | 99:1.0 | less greasy, more flowery, rounder, more natural, more jasmine like |
| para tert.-butyl-cyclohexanone (M = 154) | Ketone | 99:1.0 | less metallic, rounder, more harmonious, more woody |
| Oryclon ® (M = 198) | Ester | 100:1.0 | less metallic, rounder, more harmonious, fresher, stronger |

7. Formulation Examples

The perfume oils P1, P2, P3, P4 or P5 according to the invention from the above perfume oil examples 1 to 5 (i.e. with compound of formula (I) to be used according to the invention) were incorporated separately into the following formulations (products).

The olfactory effects described above for the respective perfume oil were also observed in the following formulations.

Example F1-Laundry Detergent Powder

| Material | Chemical Name | Function | Weight % | Weight % |
|---|---|---|---|---|
| Sodium metasilicate pentahydrate | Sodium metasilicate pentahydrate | | Ad 100 | Ad 100 |
| Sodium hydrogen carbonate | Sodium hydrogen carbonate | Alkali | 15.0 | 15.0 |
| Sodium percarbonate | Sodium carbonate peroxyhydrate | Bleaching agent | 15.0 | 15.0 |
| Peractive AC Blue | TAED/Sodium carboxymethyl cellulose | Activator | 5.00 | 5.00 |
| Genapol OA-080 | OxoAlcohol C14-15. 8EO | Nonionic surfactant | 3.00 | 3.00 |
| Texapon K12 Powder | Sodium lauryl sulphate C12 | Anionic surfactant | 7.00 | 7.00 |
| Tinopal CBS-X | | Brightener | 0.50 | 0.50 |
| Savinase 6.0 T, Type W | Protease | Enzyme | 0.40 | 0.40 |
| Termamyl 120 T | Alpha-Amylase | Enzyme | 0.30 | 0.30 |
| Sodium sulphate | Sodium sulphate | Filler | 5.50 | 5.50 |
| Perfume oil P1, P2, P3, P4 respectively. P5 | | Perfume (Fragrance) | 0.30 | 0.50 |

Example F2-all-Purpose Cleaner

| Material | Chemical Name | Function | Weight % | Weight % |
|---|---|---|---|---|
| Deionized water | Water | Solvents | Ad 100 | Ad 100 |
| Mergal K9N | 5-Chloro-2-methyl-3-(2H)-isothiazolone and 2-methyl-3-(2H)-isothiazolone | Preservative | 0.1 | 0.1 |
| Tri sodium citrate dihydrat | Tri sodium citrate dihydrate | Complexing agent | 3.0 | 3.0 |
| Zetesol NL-2 | Fatty alcohol C12-14-sulfate, sodium | Anionic surfactant | 30.0 | 30.0 |
| Imbentin C/125/055 | Fatty alcohol C12-C15, 8EO | Nonionic surfactant | 5.0 | 5.0 |
| Ethanol | Ethanol | Solvent | 2.0 | 2.0 |
| Perfume oil P1, P2, P3, P4, resp. P5 | | Perfume (fragrance) | 0.3 | 0.5 |

Example F3-Shampoo

| Material | INCI name | Weight % | Weight % |
|---|---|---|---|
| Deionized water | Water | Ad 100 | Ad 100 |
| Plantacare PS 10 | Sodium laureth sulfate, lauryl glucoside | 20.0 | 20.0 |
| Euperlan PK 771 | Glycol distearate, sodium lauryl sulfate, cocamide MEA, laureth-10 | 6.0 | 6.0 |
| Dragocid liquid | Phenoxyethanol, methylparaben, ethylparaben, butylparaben, propylparaben, isobutylparaben | 0.5 | 0.5 |

-continued

| Material | INCI name | Weight % | Weight % |
|---|---|---|---|
| Sodium chloride | Sodium chloride | 1.4 | 1.4 |
| Citric acid monohydrate cristalline | Citric acid | 0.1 | 0.1 |
| Perfume oil P1, P2, P3, P4, resp. P5 | Perfume (fragrance) | 0.5 | 0.8 |

Example F4-Shower Gel

| Material | INCI name | Weight % | Weight % |
|---|---|---|---|
| Deionized water | Water | Ad 100 | Ad 100 |
| Plantacare PS 10 | Sodium laureth sulfate, lauryl glucoside | 20.0 | 20.0 |
| Dragocid liquid | Phenoxyethanol, methylparaben, ethylparaben, butylparaben, propylparaben, isobutylparaben | 0.5 | 0.5 |
| Sodium chloride | Sodium chloride | 1.4 | 1.4 |
| Citric acid monohydrate cristalline | Citric acid | 1.3 | 1.3 |
| Perfume oil P1, P2, P3, P4, resp. P5 | Perfume (fragrance) | 0.5 | 0.7 |

Example F5-Fabric Softener

| Material | Chemical name | Function | Weight % | Weight % |
|---|---|---|---|---|
| Deionized water | Water | Solvent | Ad 100 | Ad 100 |
| Rewoquat WE 18 | Dialkylesterammonium-ethosulfate | Cationic surfactant | 16.6 | 16.6 |
| Mergal K9N | 5-Chloro-2-methyl-3-(2H)-isothiazolone und 2-methyl-3-(2H)-isothiazolone | Preservative | 0.10 | 0.10 |
| Dow Corning 1520 Antifoam | Polydimethyl siloxane | Defoamer | 0.30 | 0.30 |
| Magnesium chloride 1% solution | Magnesium chloride solution | consistency agent | 10.00 | 10.00 |
| Perfume oil P1, P2, P3, P4, resp. P5 | | Fragrance | 0.55 | 0.75 |

Example F6-Eau De Cologne/Eau De Toilette

| Ingredients | Weight % | Weight % |
|---|---|---|
| Perfume oil P1, P2, P3, P4, resp. P5 | 5 | 10 |
| Ethanol | Ad 100 | Ad 100 |
| Water | 18 | 10 |

Example F7-Aerosol Pump Spray

| Ingredients | Weight % | Weight % |
|---|---|---|
| Perfume oil P1, P2, P3, P4, resp. P5 | 1.0 | 1.5 |
| Ethanol | Ad 100 | Ad 100 |
| Water | 5.0 | 8.0 |
| Alpha tocopherol | 0.20 | 0.20 |
| Hydroxypropyl cellulose | 0.20 | — |
| Rosemary extract, soluble in ethanol | 0.22 | — |
| Cetyl alcohol | 1.00 | 0.50 |

Example F8-Shampoo

| Ingredients | Weight % | Weight % | Weight % |
|---|---|---|---|
| Sodium lauryl ether sulfate (e.g. Texapon NSO, Cognis Deutschland GmbH) | 12 | 12 | 12 |
| Cocamidopropyl betaine (e.g. Dehyton K, Cognis Deutschland GmbH) | 2 | 2 | 2 |
| Sodium chloride | 1.4 | 1.4 | 1.4 |
| Citric acid | 1.3 | 1.3 | 1.3 |
| Phenoxyethanol, methyl-, ethyl-, butyl-and propylparabene | 0.5 | 0.5 | 0.5 |
| Perfume oil P1, P2, P3, P4, resp. P5 | 0.3 | 0.5 | 0.7 |
| Water | Ad 100 | Ad 100 | Ad 100 |

Example F9-Laundry Detergent Powder

| Ingredients | Weight | Weight % | Weight % |
|---|---|---|---|
| Linear sodium alkylbenzene sulfonate | 8.8 | 8.8 | 8.8 |
| Ethoxylated fatty alcohol C12-18 (7 EO) | 4.7 | 4.7 | 4.7 |
| Na-Soap | 3.2 | 3.2 | 3.2 |
| Defoamer DOW CORNING(R) 2-4248S POWDERED ANTIFOAM, Silicone oil on zeolite as carrier material | 3.9 | 3.9 | 3.9 |
| Zeolite 4A | Ad 100 | Ad 100 | Ad 100 |
| Sodium carbonate | 11.6 | 11.6 | 11.6 |
| Sodium salt of a copolymer of acrylic acid and maleic acid (Sokalan CP5) | 2.4 | 2.4 | 2.4 |
| Sodium silicate | 3.0 | 3.0 | 3.0 |
| Carboxymethyl cellulose | 1.2 | 1.2 | 1.2 |
| Dequest 2066([[(phosphonomethyl)imino]bis[(ethylene nitrilo)bis (methylene)]]tetrakis-phosphonic acid, sodium salt) | 2.8 | 2.8 | 2.8 |
| Optical brightener | 0.2 | 0.2 | 0.2 |
| Sodium sulfate | 6.5 | 6.5 | 6.5 |
| Protease | 0.4 | 0.4 | 0.4 |
| Sodium perborate tetrahydrate | 21.7 | 21.7 | 21.7 |
| Perfume oil P1, P2, P3, P4, resp. P5 | 0.25 | 0.35 | 0.5 |
| EDTA | 1.0 | 1.0 | 1.0 |

Example F10-Liquid Laundry Detergent

| Ingredients | Weight % |
|---|---|
| Deionized water | 39.9 |
| Optical brightener | 0.10 |

-continued

| Ingredients | Weight % |
|---|---|
| Coconut fatty acids (C12-C18) | 7.5 |
| Potassium hydroxide 50% solution | 4.3 |
| Propane-1,2-diol | 5.00 |
| Fatty alcohols C12-C15, 8EO | 12.0 |
| Sodium salt of secondary alkyl sulfonates (C13-C17) | 17.0 |
| Triethanolamine | 2.0 |
| Trisodium citrate dihydrate | 5.0 |
| Dequest 2066([[(phosphonomethyl)imino]bis[(ethylene nitrilo)bis (methylene)]]tetrakis-phosphonic acid, sodium salt) | 3.0 |
| Ethanol | 3.0 |
| Enzymes | 0.7 |
| Perfume oil P1, P2, P3, P4, resp. P5 | 0.5 |

Example F11-Liquid Laundry Detergent Concentrate

| Ingredients | Weight % |
|---|---|
| Deionized water | 13.4 |
| Coconut fatty acids (C12-C18) | 10.0 |
| Fatty alcoholsC12-C15, 8 EO | 26.0 |
| Sodium salt of secondary alkyl sulfonates (C13-C17) | 26.5 |
| Triethanolamine | 8.5 |
| Sodium salt of fatty alcohol sulphatesC12-C14 | 3.0 |
| Ethanol | 5.5 |
| Urea | 4.5 |
| Enzymes | 0.9 |
| Citric acid | 1.0 |
| Perfume oil P1, P2, P3, P4, resp. P5 | 0.7 |

8. Further Perfume Oil Examples

A.

| | |
|---|---|
| AGRUMEX LC | 5 |
| ALDEHYDE C14 SOG | 1 |
| ALDEHYDE C18 SOG. 10% DPG | 1 |
| ALLYLHEPTYLAT 10% DPG | 1 |
| AMBERWOOD ® F 10% DPG | 5 |
| AMBROXIDE | 3 |
| ANISALDEHYDE FG | 1.5 |
| BENZYL ACETATE 10% DPG | 3 |
| BENZYL SALICYLATE | 30 |
| BUTYL ACETATE 10% DPG | 1 |
| CABREUVA OIL | 2 |
| CEDAR WOOD OIL VIRGINIA | 20 |
| CITRONELLOL 950 | 8 |
| CUMARIN | 10 |
| CYCLOGALBANAT ® 10% DPG | 2 |
| DAMASCON ALPHA 10% DPG | 5 |
| DAMASCONE DELTA 10% DPG | 3 |
| DECALACTON GAMMA | 2 |
| DIMETHYL BENZYL CARBINYL BUTYRATE | 2 |
| DIPROPYLEN GLYCOL | 12.5 |
| ETHYLCAPRONAT 10% DPG | 2 |
| ETHYLENE BRASSYLATE | 45 |
| ETHYLLINALOOL | 22 |
| ETHYLVANILLIN | 5 |
| EUGENOL NAT. | 1 |
| FLOROSA | 66 |
| GALAXOLID 50% IN DPG | 120 |
| HEDION | 135 |
| HELIOTROPIN/PIPERONAL | 4 |
| HEXENOL CIS-3 10% DPG | 2 |
| HEXENYL ACETATE CIS-3 10% DPG | 2 |
| HEXENYL SALICYLAT CIS-3 | 4 |

-continued

| | |
|---|---|
| HEXYL ACETATE 10% DPG | 1 |
| HEXYL ISOBUTYRATE 10% DPG | 1 |
| HEXYL SALICYLATE | 4 |
| INDOFLOR ® CRIST. | 3 |
| IONON BETA | 6 |
| IRALDEIN GAMMA COEUR 262654 | 50 |
| ISO E SUPER | 200 |
| ISOAMYL ACETATE 10% BB | 1 |
| ISOEUGENOL ACETATE | 3 |
| CRESOL METHYL ETHER PARA | 1 |
| LEAFOVERT ® 10% DPG | 5 |
| LINALOOL | 20 |
| MACROLIDE ® SUPRA | 15 |
| MANZANATE 10% DPG | 1 |
| METHYL BENZOATE 10% DPG | 1 |
| PERANAT | 6 |
| PEPPERMINT OIL PIP. CRYSTAL WHIT 10% DPG | 5 |
| PHENIRAT ® | 2.5 |
| PHENYLETHYL ALCOHOL 10% DPG | 5 |
| PHENYLETHYL ISOBUTYRATE 10% DPG | 3 |
| POLYSANTOL 10% DPG | 2 |
| ROSE OXIDE HIGH CIS 10% DPG | 1 |
| SANDRANOL ® | 25 |
| STYROLYL ACETATE | 1.5 |
| TERPIN OIL ALPHA | 30 |
| CINNAMIC ALDEHYDE 10% DPG | 1 |

By adding 1% of tricyclo[5.2.1.0]-decane-8-ethyl ether, the mixture becomes stronger, greener, fresher and the mixture gets a natural overall impression.

B.

| | |
|---|---|
| AGRUMEX LC | 120 |
| ALDEHYDE C14 SOG | 30 |
| ALLYLCYCLOHEXYL PROPIONATE | 10 |
| ALLYLHEPTYLAT | 40 |
| BENZYL ALCOHOL DD | 40 |
| CITRAL 95 | 17 |
| CITRONELLOL 950 | 4 |
| DAMASCENONE 10% DPG | 2 |
| DAMASCON BETA | 0.5 |
| DAMASCONE DELTA | 10 |
| DECALACTONE GAMMA | 5 |
| DIPROPYLENE GLYCOL | 281.5 |
| DYNASCONE 10% DPG | 2 |
| ETHYLBUTYRATE | 4 |
| ETHYLMALTOL | 10 |
| ETHYLMETHYLBUTYRATE-2 | 20 |
| FRAMBINON ® | 5 |
| GERANIOL SUPRA | 25 |
| HEDION | 5 |
| HERBAFLORATE | 15 |
| HEXYL ACETATE | 2 |
| HEXYL ISOBUTYRATE | 10 |
| HEXYL CINNAMIC ALDEHYDE ALPHA | 35 |
| IONON BETA | 65 |
| JASMAPRUNATE | 20 |
| LINALOOL | 110 |
| LINALYL ACETATE | 10 |
| MANZANATE | 7 |
| METHYLMETHYL BUTYRATE-2 | 5 |
| STYROLYL ACETATE | 30 |
| THIOMENTHANONE-8,3/1% IN TEC 10% DPG | 15 |
| UNDECAVERTOL/GIV | 25 |
| VERTOCITRAL | 20 |

By adding 1% of tricyclo[5.2.1.0]-decane-8-ethyl ether, the mixture becomes stronger, fresher and more radiant, and the composition has a fuller top note.

C.

| | |
|---|---|
| AGRUMEX HC | 110 |
| ALDEHYDE C18 SO-CALLED | 5 |
| ALLYL CYCLOHEXYL PROPIONATE | 10 |
| APRIFLOREN ® | 20 |
| BENZALDEHYDE DD | 2 |
| BENZYL BUTYRATE | 10 |
| CINNAMIC ALDEHYDE | 5 |
| CITRONELLOL 950 | 15 |
| CLARITONE ® | 15 |
| COUMARONE | 2 |
| DAMASCENONE 10% DPG | 5 |
| DIETHYL MALONATE | 95 |
| DIMETHYL BENZYL CARBINYL ACETATE | 20 |
| DIMETHYL BENZYL CARBINYL BUTYRATE | 50 |
| DOWANOL DPM | 260 |
| ETHYL BUTYRATE | 1 |
| ETHYL MALTOL | 2 |
| ETHYL VANILLIN | 2 |
| FILBERTONE 1% DPG | 5 |
| FLOROPAL | 4 |
| GLOBALIDE ® | 4 |
| HEXENYL ACETATE CIS-3 | 1 |
| HEXENYL BUTYRATE CIS-3 | 1 |
| HEXYL ACETATE | 25 |
| ISOAMYL BUTYRATE | 5 |
| JASMAPRUNAT | 8 |
| LINALOOL | 60 |
| MAGNOLAN | 6 |
| MANZANATE | 10 |
| MELONAL ® | 1 |
| METHYL OCTIN CARBONATE 10% DPG | 1 |
| PARMANYL ® 10% DPG | 4 |
| RASPBERRY AROMABASE | 15 |
| ROSE OXIDE HIGH CIS 10% DPG | 4 |
| STYRALYL ACETATE | 5 |
| VERTACETAL ® COEUR | 2 |
| VERTOCITRAL | 10 |

By adding 1% of tricyclo[5.2.1.0]-decane-8-ethyl ether, the mixture becomes rounder, fresher and has more natural aspects.

9. Exemplary Instructions for Producing Tricyclo[5.2.1.0]Decane-8-Ethyl Ether

Stage 1: Addition of ethanol to dicyclopentadiene

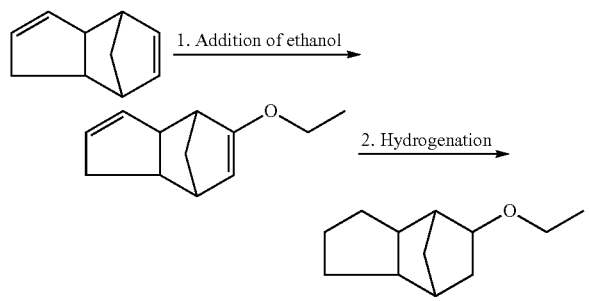

53 g Amberlyst 15 dry and 120 g ethanol are placed in a 500 ml three-necked flask with stirrer, contact thermometer, mushroom heating hood, dropping funnel. 160 g (1.21 mol) Dicyclopentadiene is then added while stirring at RT and stirred for 8-9 h at 80° C. After cooling to RT, the catalyst is filtered off and it is washed with ethanol. The mixture is alkalified with solid soda and concentrated. The residue is distilled at the ball tube (boiling range: 60-90° C./1.5 mbar). 180 g distillate is obtained.

Stage 2: Hydrogenation 180 g of the 1st stage in 700 g ethanol are hydrogenated with 10 g palladium 5% on A-carbon at 10 bar and 75° C. When the reaction is complete, the catalyst is filtered off and it is concentrated. The raw yield of 180 g is distilled at a 40 cm M.F.K. Yield 165 g corresponds to 79.6% percent of theory. The product comprises the following isomers:

Isomer I 1.9%
Isomer II 83.0%
Isomer III 0.3%
Isomer IV 12.3%

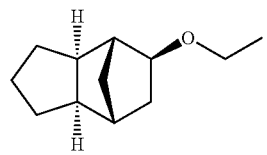

Isomer II

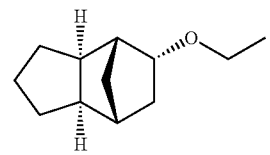

Isomer I

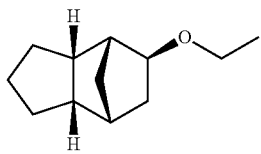

Isomer IV

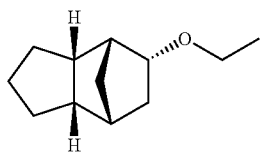

Isomer III

MS: m/z (%)=180 (2-5), 134(100), 119(55-60), 106(31-34), 91(23-24), 79(31-33), 67(22-30), 41(15-19)

The invention claimed is:
1. A fragrance mixture comprising:
(a) a compound of formula (I)

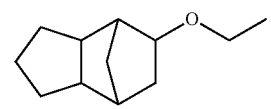

and additionally:
(b) one or more fragrance(s) selected from the group consisting of alcohols and aldehydes, having a molecular weight of 210 g/mol or less, and/or
(c) one or more fragrance(s) selected from the group consisting of ketones, ethers, and esters, having a molecular weight in the range of 190 g/mol to 250 g/mol;
wherein the mass ratio of the total amount of the fragrance(s) of (b) to the total amount of the compound of formula (I) is greater than or equal to 99:1, and/or the mass ratio of the total amount of the fragrance(s) of (c) to the total amount of the compound of formula (I) is greater than or equal to 99:1.

2. The fragrance mixture according to claim 1, wherein the component (b) comprises two or more different fragrances; and/or the component (c) comprises two or more different fragrances.

3. The fragrance mixture according to claim 1, wherein the one or more fragrances of the component (b) each have a molecular weight in the range of 140 to 170 g/mol.

4. The fragrance mixture according to claim 1, wherein the one or more fragrances of the component (c) are selected from the group consisting of methyl dihydrojasmonate, benzylsalicylate, cis-3-hexenyl salicylate, isoamyl salicylate, hexyl salicylate, 2,3,8,8-tetramethyl-1,2,3,4,5,6,7,8-octahydro-2-naphthalenylmethylketone, linalyl acetate, ethyllinalyl acetate, cedryl methyl ether, cedryl methyl ketone, cedryl acetate, (4aR,5R,7aS,9R)-octahydro-2,2,5,8,8,9a-hexamethyl-4H-4a,9-methano azuleno(5,6-d)-1,3-dioxole), 1',1',5',5'-tetra methyl-hexahydro-spiro[1.3-dioxolane-2.8' (5'H)-2H-2.4a]methanonaphthalene, cyclododecyl methyl ether, (ethoxymethoxy)cyclododecane, decahydro-betanaphthyl acetate, 4,7-methano-3a,4,5,6,7,7a-hexahydro-5(-6)-indenyl acetate, allyl-3-cyclohexyl propionate, allyl cyclohexyloxy acetate, benzylbenzoate, benzylcinnamate, oxacyclohexa-decan-2-one, 15-hydroxy-pentadecanonic acid lactone, 5-cyclohexadecen-1-one, 3-methyl-cyclopentadecenone, 1,3,4,6,7,8-hexahydro-4,6,6,6,7,8,8-hexamethyl, cyclopenta[g]-2-benzopyran, 2-[1-(3,3-dimethylcyclohexyl)ethoxy]-2-methyl-,1-propanoate, 1,4-dioxacycloheptadecane-5,17-dione, 3-methycyclopentadecanone, 8-cyclohexadecen-1-one, 3a,6,6,9a-tetramethyl dodecahydronaphtho[2,1-b]furan, alpha-iron, beta-iron, alpha-n-methylionone, beta-n-methylionone, alpha-isomethylionone, beta-isomethylionone and allylionone, and/or wherein the one or more fragrances of the component (b) are selected from the group consisting of 2-methyl-3-(4-tert-butylphenyl)propanal, 4-(4-hydroxy-4-methylpentyl)-3-cyclohexenecarboxaldehyde, 2-methyl-4-(2,2,6-trimethyl-1-cyclohexen-1-yl)-2-butenal, 1-Methyl-4-(4-methyl-3-penten-1-yl)-3-cyclohexene carboxaldehyde, 3-(3-isopropyl-phenyl)-butyraldehyde, (E)-2,6,10-trimethyl-undeca-5,9-dienal, benzo[1,3]dioxole-5-carbaldehyde, 2,2-dimethyl-3-phenyl-propan-1-ol, 2,2-Dimethyl-3-m-tolyl-propan-1-ol, 1-(4-isopropyl-cyclohexyl)-ethanol, (4-isopropyl-cyclohexyl)-methanol, 2-phenyl-ethanol, 2-isobutyl-4-methyl-tetrahydro-pyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylenoct-7-en-2-ol and (E/Z)-3,7-dimethyl-nona-1,6-dien-3-ol.

5. A method for producing a fragrance mixture according to claim 1 comprising mixing the component (a) with the component (b) and/or with the component (c).

6. The fragrance mixture according to claim 1 that is a perfume oil.

7. The fragrance mixture according to claim 1 comprising the component (b).

8. The fragrance mixture according to claim 7, wherein the mass ratio of the total amount of the fragrance(s) of the component (b) to the total amount of the compound of formula (I) is greater than or equal to 99.9:0.1.

9. The fragrance mixture according to claim 1 comprising the component (c).

10. The fragrance mixture according to claim 9, wherein the mass ratio of the total amount of the fragrance(s) of the component (c) to the total amount of the compound of formula (I) is greater than or equal to 99.9:0.1.

11. A method of enhancing a natural freshness and/or radiance and/or masking or reducing greasy, technical and/or metallic notes of one or more fragrances other than a compound of formula (I) comprising:

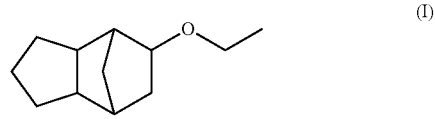

mixing the one or more fragrances other than the compound of formula (I) with an amount of the compound of formula (I) sufficient to enhance the natural freshness and/or radiance of the one or more fragrances other than the compound of formula (I) and/or to mask or reduce greasy, technical and/or metallic notes;
wherein the one or more fragrances other than the compound of formula (I) are selected from:
(b) one or more fragrance(s) selected from the group consisting of alcohols and aldehydes, having a molecular weight of 210 g/mol or less, and/or
(c) one or more fragrance(s) selected from the group consisting of ketones, ethers, and esters, having a molecular weight in the range of 190 g/mol to 250 g/mol;
wherein the mass ratio of the total amount of the fragrance(s) of (b) to the total amount of the compound of formula (I) is greater than or equal to 99:1, and/or the mass ratio of the total amount of the fragrance(s) of (c) to the total amount of the compound of formula (I) is greater than or equal to 99:1.

12. A perfumed product comprising a fragrance mixture according to claim 1 in a sensory effective amount.

13. The perfumed product according to claim 12, wherein the product is selected from the group consisting of: perfume extracts, eau de parfums, eau de toilettes, shaving lotions, eau de colognes, pre-shave products, splash colognes, perfumed refreshing wipes, acidic, alkaline and neutral detergents, textile fresheners, ironing aids, liquid laundry detergents, powdered laundry detergents, laundry pre-treatment agents, fabric softeners, laundry soaps, laundry tablets, disinfectants, surface disinfectants, air fresheners, aerosol sprays, waxes and polishes, body care products, hand creams and lotions, foot creams and lotions, depilatory creams and lotions, after-shave creams and lotions, tanning creams and lotions, hair care products, deodorants and antiperspirants, decorative cosmetic products, candles, lamp oils, incense sticks, insecticides, repellents and fuels.

14. A method of producing a perfumed product comprising:
(i) providing a fragrance mixture according to claim 1 in a sensory effective amount,
(ii) providing one or more other components of the perfumed product to be produced; and
(iii) contacting or mixing the one or more other components provided in (ii) with a sensory effective amount of the fragrance mixture provided in (i).

15. A perfumed product comprising 0.1 to 5 wt. %, based on the total weight of the perfumed product, of a fragrance mixture comprising:
(a) a compound of formula (I)

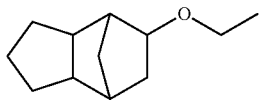

and additionally:
(b) one or more fragrance(s) selected from the group consisting of alcohols and aldehydes having a molecular weight of 210 g/mol or less, and/or
(c) one or more fragrance(s) selected from the group consisting of ketones, ethers, and esters, having a molecular weight in the range of 190 g/mol to 250 g/mol,
wherein the mass ratio of the total amount of the fragrance(s) of (b) to the total amount of the compound of formula (I) is greater than or equal to 99:1, and/or the mass ratio of the total amount of the fragrance(s) of (c) to the total amount of the compound of formula (I) is greater than or equal to 99:1.

16. The perfumed product according to claim 15 comprising 0.25 to 3 wt. %, based on the total weight of the perfumed product, of the fragrance mixture.

17. The perfumed product according to claim 15, wherein the perfumed product is a laundry detergent, a cleaning product, a hygiene or care product for the body and/or hair, or a cosmetic product.

18. A method for producing the perfumed product of claim 15, the method comprising:
I) providing one or more components of the perfumed product to be prepared which are not the components (a), (b) or (c) of the fragrance mixture,
II) mixing the one or more components provided in I) with the component (b) and/or the component (c), and
III) contacting or mixing the mixture produced in II) with an amount of the compound of formula (I) of the component (a) sufficient to enhance a natural freshness and/or radiance of the one or more fragrances of the component (b) and/or the component (c) and/or to mask or reduce greasy, technical and/or metallic notes.

* * * * *